US006648857B1

United States Patent
Pedigo

(10) Patent No.: US 6,648,857 B1
(45) Date of Patent: Nov. 18, 2003

(54) DISPOSABLE NEEDLE STICK PREVENTION AID TO PREVENT NEEDLE STICK INJURY

(76) Inventor: Barbara K. Pedigo, 1541 S. Vine St., Denver, CO (US) 80210

( * ) Notice: Subject to any disclaimer, the term of this patent is extended or adjusted under 35 U.S.C. 154(b) by 0 days.

(21) Appl. No.: 10/173,364

(22) Filed: Jun. 17, 2002

Related U.S. Application Data

(63) Continuation-in-part of application No. 09/621,370, filed on Jul. 21, 2000.

(51) Int. Cl.[7] ............................................. A61M 5/32
(52) U.S. Cl. .................................... 604/192; 604/263
(58) Field of Search ............................. 604/192, 116, 604/263; 206/365

(56) References Cited

U.S. PATENT DOCUMENTS

| | | | | | |
|---|---|---|---|---|---|
| 4,559,042 | A | * | 12/1985 | Votel | 604/192 |
| 4,573,975 | A | * | 3/1986 | Frist et al. | 604/192 |
| 4,717,386 | A | * | 1/1988 | Simmons | 604/192 |
| 4,781,697 | A | * | 11/1988 | Slaughter | 604/192 |
| 4,840,618 | A | * | 6/1989 | Marvel | 604/192 |
| 4,892,525 | A | * | 1/1990 | Hermann et al. | 604/192 |
| 4,900,309 | A | * | 2/1990 | Netherton et al. | 336/192 |
| 4,919,656 | A | * | 4/1990 | Bracker et al. | 604/192 |
| 4,981,476 | A | * | 1/1991 | Aichlmayr et al. | 604/192 |
| 4,986,816 | A | * | 1/1991 | Steiner et al. | 604/192 |
| 5,607,403 | A | * | 3/1997 | Kretzschmar et al. | 604/192 |
| 6,488,666 | B1 | * | 12/2002 | Geist | 604/263 |

FOREIGN PATENT DOCUMENTS

| | | | | |
|---|---|---|---|---|
| FR | | 2 620 339 A1 | * 3/1989 | 604/263 |

* cited by examiner

Primary Examiner—Thomas Denion
Assistant Examiner—Thai-Ba Trieu
(74) Attorney, Agent, or Firm—Edwin H. Crabtree; Ramon L. Pizarro; Donald W. Margolis

(57) ABSTRACT

A disposable needle stick prevention aid used to protect a health care provider during capping of needles and during disposal of needles. The prevention aid includes a protective shield with a center hole therein for receiving a needle cap in a press fit. The protective shield is a medical grade, sterilizable paperboard or plastic puncture resistant barrier. On a front face of the shield is a multi-colored target disposed around the center hole. The target provides focal point for capping a used needle. The protective shield includes angular sides disposed around its periphery to prevent the shield and attached needle cap from rolling freely on a flat surface. This feature facilitates a "scoop" recapping technique and minimizes cross-contamination by a used needle. The needle stick prevention aid also provides needle stick protection to dental sterilization workers when removing a used dental needle from a metal reusable dental syringe and the other end of the used needle is exposed. The shield stays attached to the needle cap with the needle container therein for protection when disposing in a biohazard container.

19 Claims, 1 Drawing Sheet

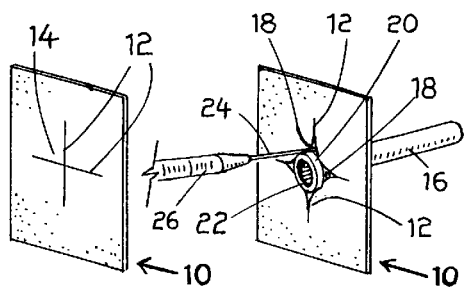
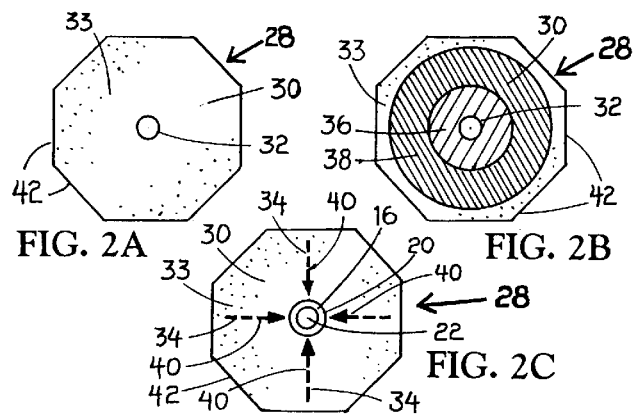
FIG. 1A (PRIOR ART)  FIG. 1B (PRIOR ART)
FIG. 2A  FIG. 2B  FIG. 2C
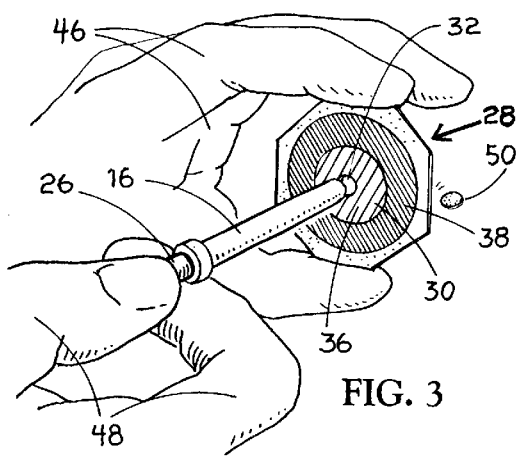
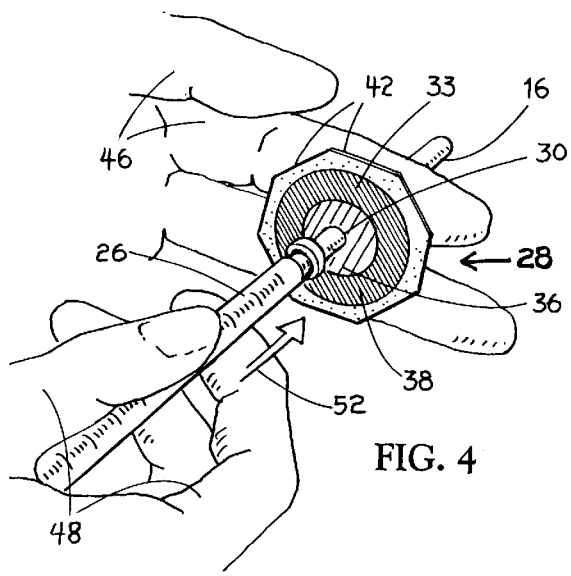
FIG. 3  FIG. 4
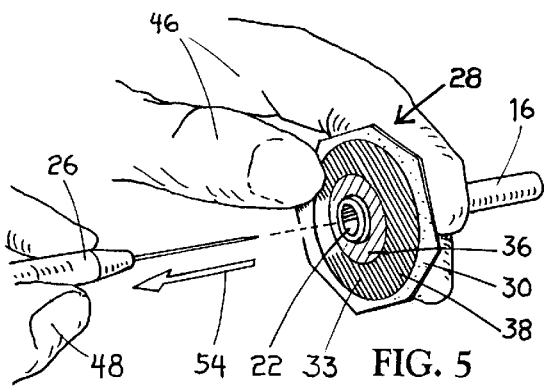
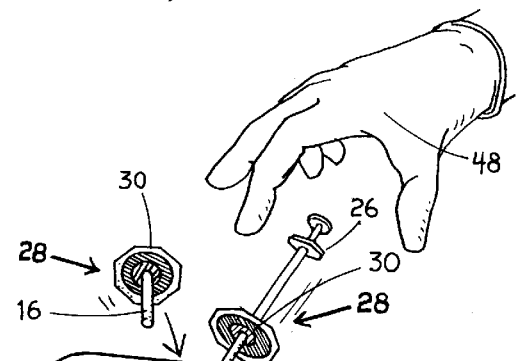
FIG. 5
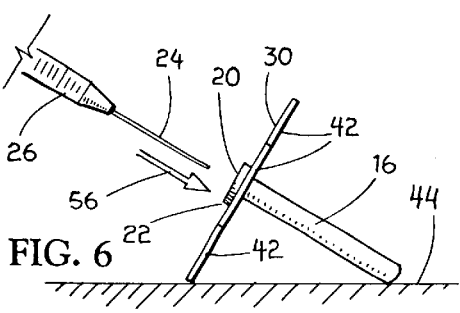
FIG. 6  FIG. 7

DISPOSABLE NEEDLE STICK PREVENTION AID TO PREVENT NEEDLE STICK INJURY

This application is a Continuation-In-Part application based on an earlier filed Application having Ser. No. 09/621,370, filed on Jul. 21, 2000 by the subject inventor.

BACKGROUND OF THE INVENTION (a) Field of the Invention

This invention relates to a device for preventing needle stick injury and more particularly, but not by way of limitation, to a disposable needle stick prevention aid for engaging a needle cap in a press fit. The needle cap can be used with a dental or medical needle attached to a syringe.

(b) Discussion of Prior Art

A NIOSH/CDC (OSHA) (Center for Disease Control) report an estimated 800,000 needle stick injuries per year. Obviously, needle stick is a serious health concern in the United States and the report suggests the use of some type of recapping device to prevent these types of injuries.

Heretofore, there have been a variety of different types of protective devices used to prevent needle stick from a contaminated needle. The needle attached to a syringe is used for an injection of a fluid into a human or animal body. When performing an injection, a health care provider must focus intensely using near vision on the injection site opening. While each needle is covered with a protective needle cap, the cap has to be removed prior to an injection.

After the injection, the health care provider must then recap the needle into a very small needle cap of less than ⅜ inch. Therefore, inserting the used needle back into the protection cap is not easy and needle stick accidents occur as mentioned above. Also after the injection, the needle may or may not be contaminate d with a life threatening virus or blood disease. HIV, Hepatitis A, B and C can be inhabitants of a freshly used needle. A large percentage of the needle stick injuries reported to the CDC result in HIV or Hepatitis. Therefore, safe recapping of the used needle is extremely important prior to the disposal of the syringe, needle and cap.

In U.S. Pat. No. 5,304,148 to Lannoye et al., a needle cap with expandable shield is disclosed. The shield is incorporated into the structure of the cap and folded when packaged. When the cap is unpackaged, the shield expands outwardly to help prevent needle stick. The shield also includes a flat edge to prevent the cap and shield from rolling on a flat surface. The patents mentioned in Lannoye et al. are incorporated herein by reference.

Also, an angular shaped needle stick protective shield is currently on the market and made of sheet cardboard. The shield includes cross-hair slits or cross-hatch slits in the center of the shield. When a needle cap is pushed through the cross-hair slits, the sides of the slits expand outwardly and next to the side of the cap. This type of protective shield is flawed since gaps or spaces open up next to the slits and the side of the needle cap when the needle cap is inserted through the slits. The gaps or spaces leave sufficient openings for a contaminated needle to be receive therethrough with the possibility of an accidental needle stick on a hand holding the needle cap when recapping the needle.

None of the above mentioned prior art patents specifically disclose the unique features, structure and function of the subject disposable needle stick prevention aid as described herein.

SUMMARY OF THE INVENTION

A primary object of the subject invention is to protect a health care provider from needle stick from the start of a needle injection in a patient until the contaminated needle is safely disposed of in a biohazard waste container. The disposable needle stick prevention aid helps prevent or greatly reduce possible needle stick when recapping a contaminated needle attached to a syringe and when removing the needle from a dental syringe prior to disposal. Currently, the subject stick prevention aid is the only needle stick prevention device approved by the FDA.

Another object of the invention is the stick prevention aid is independent of the needle cap and is adapted for quickly mounting in a press fit on a medical syringe needle cap, a dental syringe needle cap and other sizes and shapes of needle caps.

Yet another object of the stick prevention aid is that the aid is made of a needle puncture resistant protective shield having a center hole focal point indicator. The protective shield includes a center hole in the center of the shield for receiving a portion of the needle cap therethrough. The center hole focal point indicator can be pair of different colored target rings disposed around the center hole, arrows pointing toward the center hole or a similar visual aid to help a health care provider with a precise recapping focal point when reinserting the needle back into an open end of the needle cap held by the shield.

A further object of the target shield is the side of the center hole is dimensioned to be received around the outer circumference of the needle cap in a press fit. This feature eliminates any gap or space between the side of the center hole and the side of the needle cap, thus preventing a contaminated needle from being inserted between the side of the center hole and needle cap.

Still another object of the invention is the stick prevention aid is inexpensive, lightweight, easy to use and is designed to be discarded with the used needle, needle cap and a medical syringe. Also in dentistry where a large dental syringe is used for delivering dental anesthetics, the used needle is unscrewed from the syringe. At this time, the contaminated needle, needle cap and protective shield are thrown away. The dental syringe is then reused with a new needle and needle cap attached thereto.

Another object of the target shield is the periphery of the shield is angular is shape to prevent the protective shield and needle cap held thereon from rolling on a flat surface, such as a bottom of an instrument tray. This feature facilitates the use of a one-handed "scoop" technique when recapping the contaminated needle thereby providing added safety in the recapping of the needle. Also, a contaminated needle is prevented from being dragged across the surface or touching the surface of the instrument tray when using the "scoop" technique, thus preventing cross-contamination.

The disposable needle stick prevention aid includes a lightweight needle protective shield with a center hole centered thereon. The center hole is used for receiving a portion of a needle cap therethrough in a press fit. On a front face or a back face of the protective shield is a center hold focal point indicator. The focal point indicator can be a target with target rings of different colors, arrows pointing toward the center hole and like visual indicators for helping the health care provider guide a used needle toward an open end of needle cap attached to protective shield. The needle protective shield also includes angular sides disposed around it's periphery. The angular sides prevent the protective shield and attached needle cap from rolling freely on a flat surface.

These and other objects of the present invention will become apparent to those familiar with various types of needle stick prevention devices when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which:

FIG. 1A is perspective view of a prior art needle stick protective shield having cross-hair slits or cross-hatch slits in the center of the shield. The cross-hair slits are designed to receive a portion of a needle cap therethrough.

FIG. 1B is another prospective view of the prior art needle stick protective shield shown in FIG. 1A with the needle cap received through the cross-hair slits with gaps or spaces left next to the needle cap. A needle attached to one end of a medical syringe is shown accidentally inserted through one of the gaps in the shield.

FIG. 2A illustrates a front view of the subject invention having a needle protective shield with a center hole therein. The center hole is dimension for receiving different diameter needle caps therethrough in press fit.

FIG. 2B illustrates another front view of the needle protective shield having a center hole focal point indicator. In this example, the focal point indicator is in the form of a target having a small first target ring and a larger second target ring.

FIG. 2C illustrates still another front view of the subject invention wherein the center hole focal point indicator is in the form of a plurality of arrows pointing toward the center hole and acting as a guide for the health care provider.

FIG. 3 is a perspective view of a human left hand holding angular sides of the protective shield. A right hand is shown gripping a portion of a syringe and using an end of a needle cap to punch out a hole insert in the center hole in the protective shield.

FIG. 4 is a perspective view of the left hand holding a back of the protective shield as the right hand pushes the needle cap through the center hole to provide a press fit therebetween. A tight press fit prevents a gap or space between the side of the center hole and the outer circumference of the needle cap.

FIG. 5 is a perspective view of the left hand holding the back of the protective shield and the needle cap. The right hand is shown holding a portion of the syringe and releasing an attached unused needle outwardly from inside the needle cap.

FIG. 6 is a side view of the stick prevention aid with the needle protective shield holding an open end of the needle cap upwardly at an angle from a flat horizontal surface for ease in performing a one-hand "scoop" technique. In this drawing, the used or contaminated needle is shown being reinserted into the needle cap without the aid of a second hand holding the needle cap.

FIG. 7 is a perspective view of the right hand dropping the used medical syringe, needle, a needle cap and an attached protective shield through an opening in the top of a biohazard waste container. Also, a used needle unscrewed from a dental syringe, a needle cap and an attached protective shield are shown being discarded into the waste container.

DETAILED DESCRIPTION OF THE PREFERRED EMBODIMENTS

In FIG. 1A, a perspective view of a prior art needle stick protective shield 10 is shown having cross-hair slits 12 or cross-hatch slits in a center 14 of the shield 10. The cross-hair slits 12 are designed to receive a portion of a needle cap 16 therethrough.

In FIG. 1B, another prospective view of the prior art needle stick protective shield 10 is shown with the needle cap 16 received through the cross-hair slits 12 with gaps 18 or spaces next to a needle cap ring 20 with an open end 22 of the needle cap 16. A needle 24 is attached to one end of a medical syringe 26 and shown accidentally inserted through one of the gaps 18 in the shield 10.

In FIG. 2A, a front view of the subject disposable needle stick prevention aid is shown having general reference numeral 28. The stick prevention aid 28 includes a protective shield 30 with a center hole 32 therein. The center hole 32 is dimensioned for receiving different diameter needle caps therethrough in press fit.

The protective shield 30 is made of lightweight cardboard or thin sheet plastic. A cardboard protective shield 30 is typically made of a non-recycled, medical grade, paperboard having a thickness in a range of 0.022 to 0.030 inches and specifically SUS 0.028 inches. This thickness has proven by demonstration to be adequate in protecting against accidental needle penetration. Also, the protective shield includes an aqueous barrier coating thereon to help prevent absorption of fluid contaminates. Further, the shield can be sterilized in an autoclave or by other sterilization techniques prior to use.

The protective shield 30 has a front face 33 and a back face. The back face is not shown in the drawings. The front face 33 or the back face have a different color than the color of the needle cap 16, so that a contrast in color is apparent when the needle cap ring 20 is disposed next to the side of the center hole 32. In this manner, the health care provider has a clear visual aid against the background of the shield 30 when recapping the needle 24 inside the needle cap 16.

In FIG. 2B, another front view of the needle protective shield 30 is shown having a center hole focal point indicator 34. In this example, the focal point indicator 34 is in the form of a target having a small first target ring 36 having a first color and a larger second target ring 38 having second color. The two rings 36 and 38 are disposed around the center hole 32.

In FIG. 2C, still another front view of the subject invention is shown wherein the center hole focal point indicator 34 is in the form of a plurality of arrows 40 pointing toward the center hole 32 and acting as a guide for the health care provider when recapping the needle 24. In this drawing, the needle cap 16 is shown inserted through the center hole 32 with the needle cap ring 22 disposed next to the side of the center hole.

While the drawings illustrate two different embodiments of the center hole focal point indicator 34, it can be appreciated that various types of visual indicator on the front or back face of the protective shield 30 can be used equally well without departing from the spirit and scope of the invention.

It should be noted that protective shield 30 includes angular sides 42 disposed around its periphery. The angular sides 42, in this example, are in a form of an octagon. While the octagon shape is shown, it can be appreciated that the shield can easily be in a form of a square, a rectangle, a hexagon and other geometric angular shapes. When the protective shield 30 rests on one of the flat sides 42, as shown in FIG. 6, the shield 30 and the attached needle cap 16 are prevented from rolling freely on a flat surface 44. The flat surface 44 may be part of a medical tray, tabletop and the like used in holding medical instruments of this type. The flat surface 44 is shown in FIG. 6.

In FIG. 3, a perspective view of a human left hand 46 with fingers is shown holding the angular sides 42 of the protective shield 30. A right hand 48 with fingers is shown gripping a portion of the syringe 26 and using a closed end of the needle cap 16 to punch out a hole insert 50 in the center hole 32 in the center of the protective shield.

In FIG. 4, a perspective view of the left hand 46 with fingers is shown holding a back of the protective shield 30 as the right hand 48 pushes, as indicated by arrow 52, a portion of the length of the needle cap 16 through the center hole 32 to provide a press fit therebetween. The needle cap 16 will normally be pushed through the center hole 32 until the needle cap ring 20 is disposed next to the front face 33 of the shield 30, as shown in FIG. 5.

A tight press fit prevents a gap or space between the side of the center hole 32 and an outer circumference of the needle cap 16. Typically the diameter of a needle cap used with a dental syringe is 8 mm. The diameter of a needle cap used with a medical syringe is 6 mm. Therefore, the diameter of the center hole 32 will correspond with the diameter of the needle cap being used, so that the press fit is insured and no gap or space is left between the side of the hole and the outer circumference of the needle cap. While the 6 mm and 8 mm diameter sizes are mentioned above, it can be appreciated that the center hole 32 can be made to fit any size needle cap diameter.

In FIG. 5, a perspective view of the left hand 46 is shown holding the shield 30 and the needle cap 16. The right hand 48 is shown holding the syringe 26 and releasing the attached needle 24 outwardly, as indicated by arrow 54, from open end 22 and the inside of the needle cap 16.

In FIG. 6, a side view of the stick prevention aid 28 is illustrated with the target shield 30 having sufficient strength and thickness for holding the open end 22 of the needle cap 16 upwardly at an angle from the horizontal flat surface 44 for ease in practicing a one-hand "scoop" technique. In this drawing, the used or contaminated needle 24 is shown being reinserted, as indicated by arrow 56, into the open end 22 of the needle cap 16, without the aid of the left hand 46 having to hold the needle cap 16 or the protective shield 30. It can be appreciated, that by using the subject invention and the one-hand "scoop" method, the chance of needle stick is eliminated since no hand or fingers are near the contaminated needle 24 as it is recapped. Also, using the subject invention, the chance of cross-contamination by dragging or contacting the contaminated needle 24 with the flat surface 44 is reduced or eliminated since the needle 24 now can be guided by the center hole focal point indicator 34 on the protective shield 30 into the needle cap 16.

In FIG. 7, a perspective view of the right hand 48 is shown dropping a used syringe 26, recapped needle 24 in a needle cap 16, and an attached protective shield 30 through an opening 58 in a top of a biohazard waste container 60. Also, a used needle 24, unscrewed from a dental syringe, a needle cap 16 and an attached protective shield 30 are shown being discarded into the waste container 60.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A disposable needle stick prevention aid adapted for engaging a portion of a needle cap, the needle cap received around a needle attached to one end of a syringe, the needle stick prevention aid comprising:

a protective shield having a center hole centered thereon, said center hole adapted for receiving a portion of the needle cap therethrough and holding the needle cap in a press fit, said protective shield including an aqueous barrier coating thereon to help prevent absorption of a fluid contaminate thereon.

2. The needle stick prevention aid as described in claim 1 further including a center hole focal point indicator on said protective shield and disposed next to said center hole, said center hole focal point indicator adapted for providing a focal point when reinserting the needle back into the needle cap.

3. The needle stick prevention aid as described in claim 2 wherein said center hole focal point indicator is a target, said target including a circular first ring around a side of said center hole and a larger circular second ring disposed next to said first ring.

4. The needle stick prevention aid as described in claim 3 wherein said first ring has a first color and said second ring has a second color for increased visibility in focusing on said center hole.

5. The needle stick prevention aid as described in claim 2 wherein said center hole focal point indicator is at least one arrow pointed toward said center hole.

6. The needle stick prevention aid as described in claim 1 wherein said protective shield includes angular sides disposed around its periphery, said angular sides preventing said protective shield and attached needle cap from rolling freely on a flat surface.

7. The needle stick prevention aid as described in claim 1 wherein said protective shield is made of cardboard having a thickness in a range of 0.022 to 0.030 inches to prevent the needle from being accidentally inserted therethrough.

8. The needle stick prevention aid as described in claim 1 wherein said center hole has a diameter corresponding with a diameter of the needle cap to insure a press fit.

9. The needle stick prevention aid as described in claim 1 wherein said protective shield is a sterilized protective shield.

10. A disposable needle stick prevention aid adapted for engaging a portion of a needle cap, the needle cap received around a needle attached to one end of a syringe, the needle stick prevention aid comprising:

a protective shield having a center hole centered thereon, said center hole having a diameter corresponding to a diameter of the needle cap, said center hole adapted for receiving a portion of the needle cap therethrough and holding the needle cap in a press fit, said protective shield including an aqueous barrier coating thereon to help prevent absorption of a fluid contaminate thereon; and a center hole focal point indicator disposed next to said center hole, said center hole focal point indicator adapted for providing a focal point when reinserting the needle back into the needle cap.

11. The needle stick prevention aid as described in claim 10 wherein said center hole has a diameter of 6 mm.

12. The needle stick prevention aid as described in claim 10 wherein said center hole has a diameter of 8 mm.

13. The needle stick prevention aid as described in claim 10 wherein said center hole focal point indicator is a target, said target including a circular first ring having a first color and disposed around a side of said center hole and a larger circular second ring having a second color and disposed next to said first ring.

14. The needle stick prevention aid as described in claim 10 wherein said center hole focal point indicator is a plurality of arrows pointed toward said center hole and spaced therearound.

15. The needle stick prevention aid as described in claim 10 wherein said protective shield includes angular sides disposed around its periphery, said angular sides preventing said protective shield and attached needle cap from rolling freely on a flat surface.

16. A sterile disposable needle stick prevention aid adapted for engaging a portion of a needle cap, the needle cap received around a needle attached to one end of a syringe, the needle stick prevention aid comprising:

a protective shield having angular sides, said protective shield made of cardboard sufficient in thickness and strength to prevent the needle from accidentally being inserted therethrough, said protective shield having a center hole centered thereon, said center hole having a diameter corresponding to a diameter of the needle cap, said center hold adapted for receiving a portion of the needle cap therethrough and holding the needle cap in a press fit and upright at an angle from the horizontal with said protective shield is resting on a flat horizontal surface, said protective shield including an aqueous barrier coating thereon to help prevent absorption of a fluid contaminate thereon; and a center hole focal point indicator on said protective shield, said focal point indicator adapted for providing a focal point when reinserting the needle back into the needle cap.

17. The needle stick prevention aid as described in claim 16 wherein said protective shield with angular sides is formed in an octagon geometric shape.

18. The needle stick prevention aid as described in claim 16 wherein said focal point indicator is a multi-colored target disposed around said center hole.

19. The needle stick prevention aid as described in claim 16 wherein said focal point indicator directs the eye toward said center hole in the center of said protective shield.

* * * * *